United States Patent [19]
Lautt et al.

[11] Patent Number: 5,561,165
[45] Date of Patent: Oct. 1, 1996

[54] METHOD FOR TREATING INSULIN RESISTANCE

[75] Inventors: W. Wayne Lautt; Y. Luke Zhang, both of Winnipeg, Canada

[73] Assignee: The University of Manitoba, Winnipeg, Canada

[21] Appl. No.: 347,884

[22] Filed: Dec. 1, 1994

[30] Foreign Application Priority Data

Dec. 1, 1993 [GB] United Kingdom ............. 932462

[51] Int. Cl.⁶ .................................................. A61K 31/13
[52] U.S. Cl. .................................... 514/667; 514/866
[58] Field of Search ............................. 514/527, 557, 514/667, 866

[56] References Cited

U.S. PATENT DOCUMENTS 5,035,887  7/1991  Ayer et al. .................... 424/473

OTHER PUBLICATIONS

The Merck Index, 9th Ed, 1976, Nos. 12, 15, 78, 79 & 5793–5795.
Blei et al., (1982), "Insulin Resistance and Insulin Receptors in Hepatic Cirrhosis." *Gastroenterology*, 83, 1191–9.
Lautt, W. W., (1980), "Hepatic Parasympathetic Neuropathy As Cause Of Maturity–Onset Diabetes?." *Gen. Pharmac.*, 11, 343–345.
Mondon, C., Burton, S., (1971), "Factors Modifying Carbohydrate Metabolism And Effect Of Insulin In Perfused Rat Liver." *Amer. J. Physiol.*, 220(3), 724–733.
Schafer et al., (1993), "Hepatic Blood Volume Responses and Compliance in Cats with Long–term Bile Duct Ligation." *Hepatology*, 18(4), 969–977.
Xie, et al., (1992), "Insulin Resistance Of Glucose Response Produced By Hepatic Denervations." *Can. J. Pharmacol.*, 71, 175–178.

*Primary Examiner*—John W. Rollins
*Attorney, Agent, or Firm*—Fish & Neave; Margaret A. Pierri

[57] ABSTRACT

A method is provided for increasing insulin responsiveness and improving glucose tolerance in a mammal comprising administration of an effective amount of a cholinergic agonist; pharmaceutical compositions are also provided.

18 Claims, 8 Drawing Sheets

METHOD FOR TREATING INSULIN RESISTANCE

This invention relates to treatment of insulin resistance in non-insulin dependent diabetics and patients with liver disease.

BACKGROUND OF THE INVENTION

Patients with non-insulin dependent diabetes mellitus (NIDDM) show insulin resistance and impaired glucose tolerance. They have also been shown to have parasympathetic neuropathies. Patients with chronic liver disease also show insulin resistance.

Currently, there is no suitable treatment for insulin resistance other than diet, exercise or weight loss which are of minimal use in liver disease and variable use in diabetes.

The present inventors developed an animal model of insulin resistance produced by nerve damage, and were able to produce insulin resistance in cats by surgical interruption of the mixed nerve bundle to the liver (Xie et al. (1993)).

They further demonstrated that the same degree of resistance could be produced by pharmacological blockade of parasympathetic nerve function using the muscarinic receptor antagonist, atropine (Xie et al., (1994), Proc. West. Pharmacol. Soc., v. 37, pp. 39–40).

Using a new animal model in the rat, the present inventors have devised a convenient method for screening compounds with therapeutic potential for treating insulin resistance. Using this screening system, the inventors have identified compounds which reduce or reverse insulin resistance.

SUMMARY OF THE INVENTION

In accordance with one aspect of the present invention, there is provided a method for increasing insulin responsiveness and improving glucose tolerance in a mammal in which insulin responsiveness and glucose tolerance are impaired comprising administering to the mammal an effective amount of a cholinergic agonist.

In accordance with another aspect of the present invention, there is provided a method for reducing insulin resistance in a mammal comprising administering to the mammal an effective amount of a cholinergic agonist.

In accordance with a further aspect of the present invention, there is provided a pharmaceutical composition for increasing insulin responsiveness and improving glucose tolerance in a mammal comprising an effective amount of a cholinergic agonist and a pharmaceutically acceptable carrier.

SUMMARY OF THE DRAWINGS

Certain embodiments of the invention are described, reference being made to the accompanying drawings, wherein.

DETAILED DESCRIPTION OF THE INVENTION

Previous studies by the inventors and others have shown that hepatic parasympathetic nerves are capable of producing an insulin-like effect with a greater and more rapid onset of response than insulin, itself, can produce (Lautt & Wong (1978)). Insulin and acetylcholine are reported to have additive effects and it is suggested that isolated liver preparations are relatively insulin resistant because of the absence of normal innervation. The inventors have previously proposed a hypothesis that parasympathetic neuropathy can lead to some forms of maturity onset diabetes (Lautt, 1980). The glucose intolerance and insulin resistance that is seen in many forms of liver disease is also likely related to selective hepatic neuropathies.

The inventors have developed a technique, using a rat model, for determining insulin resistance and conveniently and quickly assessing the effect of potential therapeutic agents on insulin resistance in a mammal.

This new rat model test, call the euglycemic clamp test, is described in Example 1.

Using this test, the inventors have developed several animal models of insulin resistance.

Insulin resistance has been produced in rats by surgical denervation of the hepatic parasympathetic nerves (Example 2), by administration of atropine (Example 4), by chronic bile duct ligation (Example 5) and by administration of carbon tetrachloride (Example 6).

Figure 6:
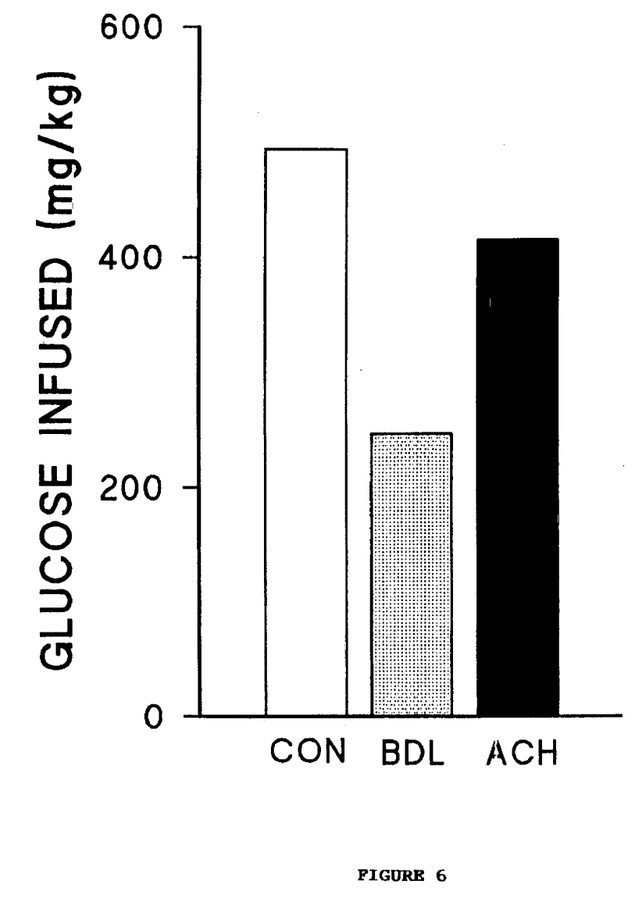
FIG. 6 shows insulin sensitivity of control (open bar), bile duct ligated (shaded bar) and acetylcholine treated (solid bar) rats.

Reversal of insulin resistance has been achieved in the three models examined, by administration of the cholinergic agonist, acetylcholine. As described in Example 3, five rats rendered insulin resistant by hepatic denervation were restored to essentially normal insulin sensitivity by administration of acetylcholine. Acetylcholine administration was also effective to partially reverse insulin resistance produced by chronic bile duct ligation, as shown in FIG. 6. Acetylcholine administration to rats with normal nerves did not produce altered insulin sensitivity, as described in Example 4.

Hepatic parasympathetic nerves have been shown to have a direct effect on hepatic glucose output. Stimulation of the vagus nerve directly (Shimazu, 1981; 1974) or indirectly by electrical stimulation of the lateral hypothalamic nucleus of rabbits (Shimazu et al., 1966) results in activation of glycogen synthetase to near maximum levels by 5 minutes following onset of stimulation. The response is independent of the pancreas. The same level of activation of synthetase by insulin is seen to occur at a much slower rate (30 minutes) (Shimazu et al., 1966). Incorporation of radioactive glucose into liver glycogen was augmented by vagal stimulation in the absence of a pancreas; glycogen deposition following glucose injection was greatly enhanced by vagal stimulation (Shimazu & Figimoto, 1971).

In an intact cat liver pretreated with intraportal 6-hydroxydopamine to eliminate hepatic sympathetic nerves (Lautt & Cote, 1976; 1977), stimulation of the remaining nerve fibres in the mixed hepatic nerve results in a rapid decrease in net hepatic glucose output reaching one-quarter of control output by 2 minutes. Output remains depressed for at least 20 minutes following cessation of stimulation (Lautt & Wong, 1978).

Absence of the hepatic parasympathetic nerves produces a liver that is much less effective in trapping glucose. Bilateral vagotomy reduces the glycogen deposition in rats; administration of acetylcholine restores the deposition rate to normal (Mondon & Burton, 1971). While this response could be attributed to an interference with reflex release of insulin, it was further shown that the lack of dramatic effect of insulin on isolated perfused livers could be overcome by concomitant administration of acetylcholine. Cholinergic stimulation and insulin given together produced a response much greater than that seen with either stimulus alone (Mondon & Burton, 1971).

Figure 2:
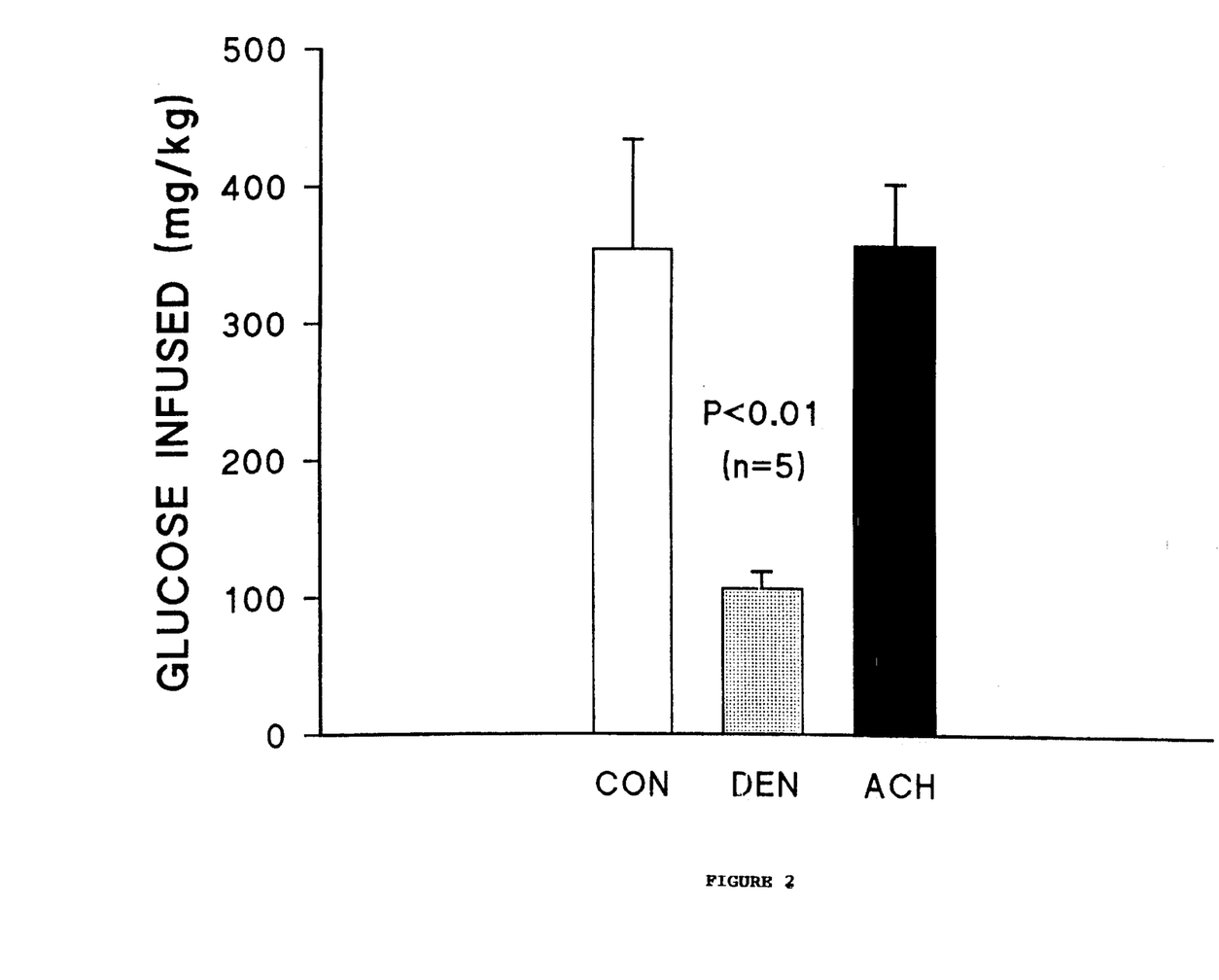
FIG. 2 shows insulin sensitivity (expressed as glucose infused in mg/kg) of control (open bar), denervated (shaded bar) and acetylcholine treated (sold bar) rats.

Thus the animal experiments indicate strongly that the parasympathetic nerves to the liver produce a rapid and dramatic decrease in hepatic glucose output accompanied by glycogen deposition. Insulin produces a minor effect on liver tissues in the absence of cholinergic stimulation. Section of hepatic nerves results in an immediate and significant (37.3±9.8%) inhibition of response to intravenous insulin (100 mU/kg) in the cat (Xie et al., 1993) and a 62.8±16.3% inhibition in the rat (FIG. 2). These livers are similar to that of the maturity-onset diabetic in that, in spite of high glucose and hyperinsulinemia, hepatic uptake of glucose is dramatically reduced.

The first comprehensive review of hepatic nerve functions (vascular, metabolic, biliary; afferent and efferent, sympathetic and parasympathetic nerves) was published in 1980 by one of the inventors (Lautt, 1980).

Hepatic denervation in the rat produced insulin resistance to 100 mU/kg of insulin. This study indicated that the effect of hepatic denervation was able to be produced in its entirety by selective surgical denervation of the hepatic anterior plexus (reaching the liver in conjunction with the hepatic artery). The much more surgically difficult denervation of the posterior plexus and surgical denervation of the vagus as well as complete hepatic denervation using topical application of phenol results in no further insulin resistance. This observation is technically extremely important because it greatly simplifies the surgical approach required to produce the acute insulin resistance. This suggests that the nerves of relevance reach the liver exclusively through the anterior plexus but does not determine whether the nerves of relevance are sympathetic, parasympathetic, or afferent in nature.

In addition, a time control study indicated that these rats were able to respond to this bolus dose of insulin with four consecutive similar responses. This type of time control is absolutely essential in order to carry out the further studies.

A review of diabetic autonomic neuropathy (Hosking et al., 1978; Brown & Asbury, 1984; Menzinger et al., 1991) indicates that autonomic neural disruption is extremely common and accounts for many of the less severe symptoms of diabetes. Most studies have examined the function of autonomic nerves in the advanced diabetics, with the aim of understanding and controlling some of the complications of diabetes. The hepatic innervation has not been studied. This is not surprising in view of the fact that intrahepatic innervation studies have lagged well behind similar studies for other systems and only relatively recently has the consensus arisen, that parenchymal cells in the liver are directly innervated (Forssmann & Ito, 1977). Nevertheless, from the data reviewed it appears clear that in the earliest stages of diabetes there is autonomic neuropathy and that "parasympathetic abnormality is the earliest manifestation of the diabetic autonomic neuropathy" (Hosking, et al., 1978). The neuropathy has been considered as secondary to diabetes but the cause of the neuropathy is unknown and, while a number of experiments will be required to demonstrate each step of the hypothesis, the circumstantial evidence is consistent with hepatic parasympathetic neuropathy as an initiating event leading to maturity-onset diabetes. Although it is well accepted that even experimentally-induced diabetes results in parasympathetic (and other) neuropathies (Yagihashi & Sima, 1986), this fact does not preclude the possibility that some forms of clinical diabetes have the neuropathy as an initiating event that leads to the metabolic disorder which then leads to further neuropathy.

The association of parasympathetic neuropathy and insulin resistance in NIDDM patients and the presentation of insulin resistance in surgically denervated rats suggests that these animals provide a suitable model for studying and treating the insulin resistance of the NIDDM patient. The reversal of insulin resistance in these nerve-damaged rats by a cholinergic agonist indicates that such agents are likely to be of therapeutic value in NIDDM patients. Cholinergic agonists include methacholine and bethanechol.

The inventors have found that administration of atropine produces the full picture of insulin resistance seen after hepatic denervation, indicating the involvement of parasympathetic nerves acting through cholinergic muscarinic receptors.

A hepatic autonomic dysfunction occurs in animal models of liver disease and these models also show insulin resistance. Further, chronic liver disease in human patients shows evidence of autonomic nerve dysfunction and insulin resistance strongly suggesting that parasympathetic nerve dysfunction accounts for the insulin resistance in these patients.

Insulin resistance has long been known to occur in cirrhotic patients and animal models (Collins et al., 1970). Methods for assessing insulin resistance have progressed but still remain debatable as to the best method (Bergman et al., 1985). More controversial is the methodology used to assess the specific tissues of resistance. The considerable differences in methodologies undoubtedly account for much of the differences in the literature. The liver has been reported as the resistant tissue (Shankar et al., 1987) and this resistance is suggested to explain most of he disturbances in glucose metabolism in cirrhosis (Creutzfeld et al., 1983; Taylor et al., 1986). On the other hand, it is claimed that the euglycemic clamp method of assessing insulin sensitivity reflects primarily (85%) estrahepatic metabolism (DeFronzo et al., 1981) that cannot be accounted for solely by the generation of hyperglycemia and/or hyperinsulinemia. The existence of an unidentified gastrointestinal hormone which potentiates insulin's action on the liver has been postulated (Lickely et al., 1975; DeFronzo et al., 1978a), and the absence of this hormone was suggested to be the initial pathological event in the maturity-onset diabetic (DeFronzo et al., 1978b). The data are, however, equally compatible with the existence of a neural potentiation of insulin's effect. The neural hypothesis (Lautt, 1980) receives support from the fact that in the absence of cholinergic stimulation, the liver becomes unable to take up glucose and this can be reversed in the intact or isolated liver by administration of acetylcholine (Mondon & Burton, 1971). Parasympathetic neuropathy would therefore be expected to result in postprandial hyperglycemia with a resultant hyperinsulinism. While a complete reflex arc has not yet been demonstrated, it is known that glucose perfused through the lumen of the small intestine produces activation of nerves in the mesenteric trunk (Sharma & Nasset, 1962) and a similar parasympathetic reflex has been shown to transiently result in pancreatic stimulation and insulin release (Fischer et al., 1972; Fisher, 1974).

Although there may be more than one mechanism contributing to insulin resistance in chronic liver disease, hepatic parasympathetic neuropathy would undoubtedly produce this effect. Hepatocytes normally receive direct cholinergic innervation (Forssmann & Ito, 1977). In human cirrhotics, an antibody to a neural axoplasmic protein was used to demonstrate a severe reduction in parenchymal cell innervation in precirrhotic livers and absent innervation in regenerating nodules of established cirrhosis (Lee et al., 1992). In the BDL model of liver disease, severe parasympathetic abnormalities were characteristics (Akiyoshi, 1989).

The inventors have also developed insulin resistance in rats as a result of chronic bile duct ligation. This insulin resistance is comparable to that seen in liver disease in humans. Acetylcholine was also effective in reducing this type of insulin resistance, indicating the likely usefulness of cholinergic agonists to treat the insulin resistance which accompanies liver disease.

Cholinergic agonists may be administered orally, subcutaneously or intravenously. Oral administration prior to each meal is preferred. A suitable dosage of a cholinergic agonist for a human may be estimated on the basis of the potency of the agonist in the rat model.

EXAMPLE 1

Euglycemic clamp test for measuring sensitivity or resistance to insulin.

This sensitive technique, developed in a rat model, permits determination of insulin resistance and provides a simple and convenient method for screening compounds of potential therapeutic value for modifying or treating insulin resistances.

Male, Sprague Dawley rats were fed regular lab chow until 18 hours prior to the acute testing. Rats were anesthetized with pentobarbital. Anesthetic level was maintained by the use of a constant intravenous drip to avoid the need for bolus administration of anesthetic during the experiment. A blood sampling shunt was established by inserting a catheter into the femoral artery which allowed blood to flow into a silicone tube and re-enter the circulation through the femoral vein. Glucose infusion was via a jugular venous catheter. Central venous pressure was monitored through the line used to administer anesthetic and fluids (fluid administration was ceased during monitoring). Systemic arterial pressure was monitored through a femoral arterial catheter. Body temperature was monitored and maintained at 37.5° C. Arterial blood samples were taken by direct puncture into the arterial venous shunt for glucose analysis. The rat received heparin to prevent clotting in the shunt. Insulin was administered at a dose of 50 mU I.V. over a 5 minute period. Glucose determinations were made every 3 minutes using a YSI Industrial Analyzer and 0.1 ml whole blood.

Time control pilot studies in the rat indicate that as many as four consecutive responses can be obtained with no statistically significant changes over an 8 hour period.

The rate of glucose infusion was adjusted using a variable rate infusion pump to maintain the blood glucose at a constant level equal to the pre-insulin level, based on measurements of blood glucose on blood samples withdrawn from the shunt at 3 minute intervals.

Figure 1:
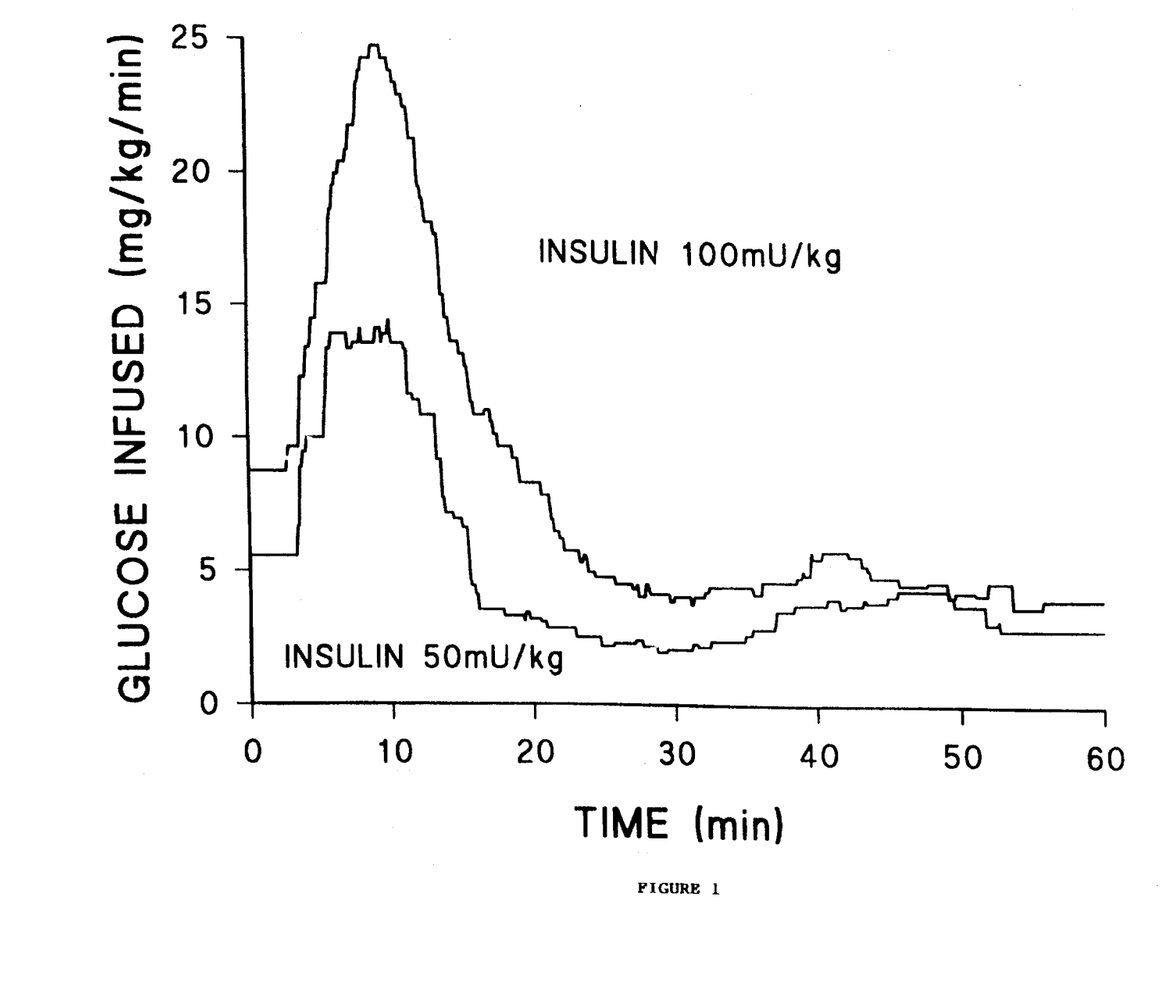
FIG. 1 shows the rate of glucose infusion over indicated time period required to maintain a constant blood glucose level after administration of 50 mU/kg or 100 mU/kg insulin.

The total amount of glucose infused over the one hour test period (mg/kg body weight) was used as the index of insulin sensitivity. The experiment was repeated after an injection of 100 mU/kg insulin. The results are shown in FIG. 1. The curves were obtained by averaging the glucose infusion rate from 11 animals at 0.1 min intervals. The maximal glucose infusion rate was at approximately 10 minutes with the responses being essentially complete by 30 mins. 493.7±60.4 mg/kg glucose was required to maintain arterial blood glucose levels constant following the administration of 100 mU/kg of insulin. In response to 50 mU/kg insulin, 269.5±45.3 mg/kg (n=9), glucose was required (p<0.01).

EXAMPLE 2

Insulin resistance produced by denervation.

5 Male Sprague Dawley rats were subjected to surgical denervation of the hepatic parasympathetic nerves.

Via laparotomy, a portal puncture was used for administration of drugs to the portal vein. The needle was held in place using tissue glue. The hepatic nerves were manipulated in the area of the common hepatic artery, just prior to the branching of this artery to form the hepatic artery proper and the gastroduodenal artery. There is approximately 1 cm of blood vessel along which the hepatic nerves are accessible either for surgical denervation or for ligation and electrical stimulation of the peripheral end. All incisions were closed using surgical clips or sutures. After 45 minutes to allow for recovery from surgical stress (previous studies demonstrated that stress hormones and glucose levels stabilised at approximately that time), the first glucose sample was taken. Samples were taken at 5 minute intervals until three successive samples showed no significant variation. At that time, the euglycemic clamp test described in Example 1 was carried out.

The results are shown in FIG. 2. Insulin sensitivity, expressed as total amount of glucose infused over the 1 hour test (in mg/kg body weight), was decreased by 62.8±16.2% in the surgically treated animals (p<0.01).

EXAMPLE 3

Reversal of insulin resistance by acetylcholine

The five rats rendered insulin resistant by hepatic denervation, as described in Example 2, were treated by administration of acetylcholine by infusion into the portal vein at a rate of 2.5 mg/kg/min beginning 10 minutes prior to insulin administration and continuing for entire 1 hour test period. Insulin sensitivity was determined as described in Example 1. The results are shown in FIG. 2. The response to insulin was returned to the pre-denervation level, indicating complete reversal of the insulin resistance.

EXAMPLE 4

Figure 3:
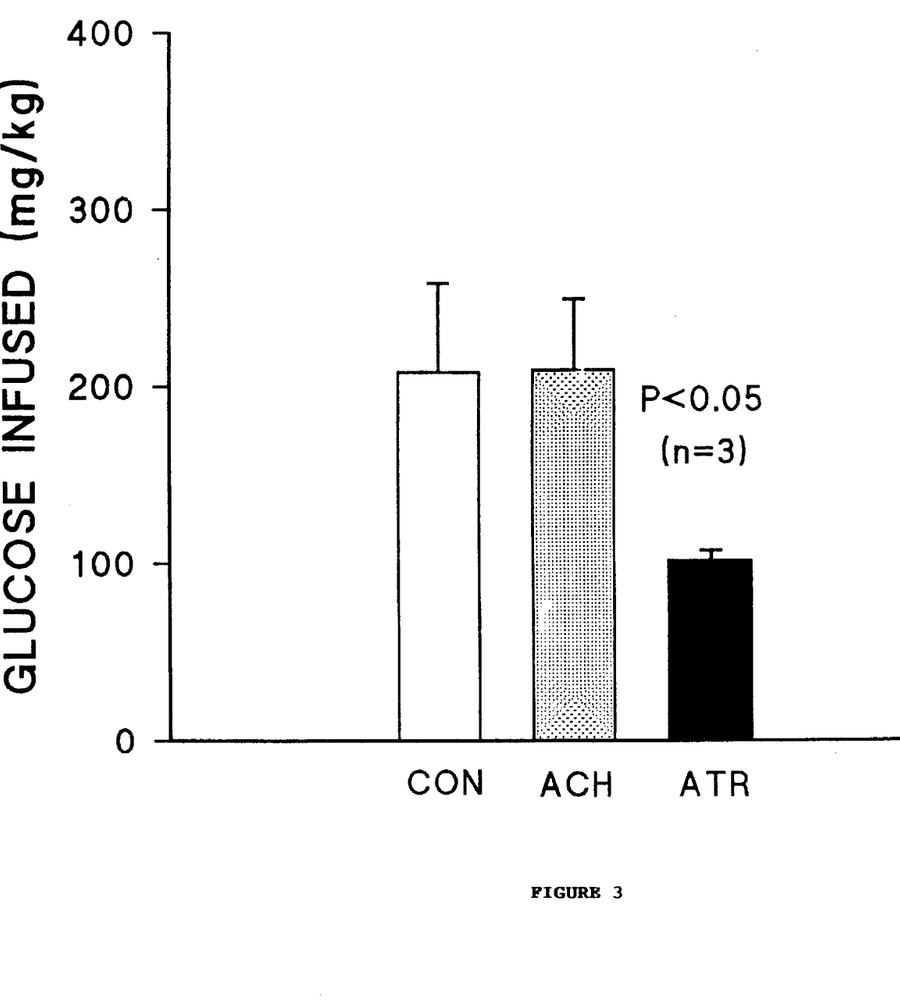
FIG. 3 shows insulin sensitivity of control (open bar), acetylcholine and atropine treated (shaded bar) and atropine treated (solid bar) rats.

Insulin resistance produced by atropine and reversed by acetylcholine 3 rats were administered 3 mg/kg atropine into the portal vein and after 10 minutes, an insulin sensitivity test was carried out as described in Example 1, after 50 mU/kg insulin. Acetylcholine was administered by infusion into the portal vein at the dosage and in the manner described in Example 3 and an insulin sensitivity test was carried out as in Example 3. As seen in FIG. 3, acetylcholine did not have an effect on insulin sensitivity in rats with normal functioning nerves. As seen in FIG. 3, mean insulin sensitivity was decreased by 45±12% by atropine treatment ($p<0.05$).

EXAMPLE 5

Insulin resistance produced by bile duct ligation.

4 rats were anesthetized, the bile duct was ligated and cut and the chronic obstructive state produced was allowed to progress into liver disease over 3 weeks.

Figure 4:
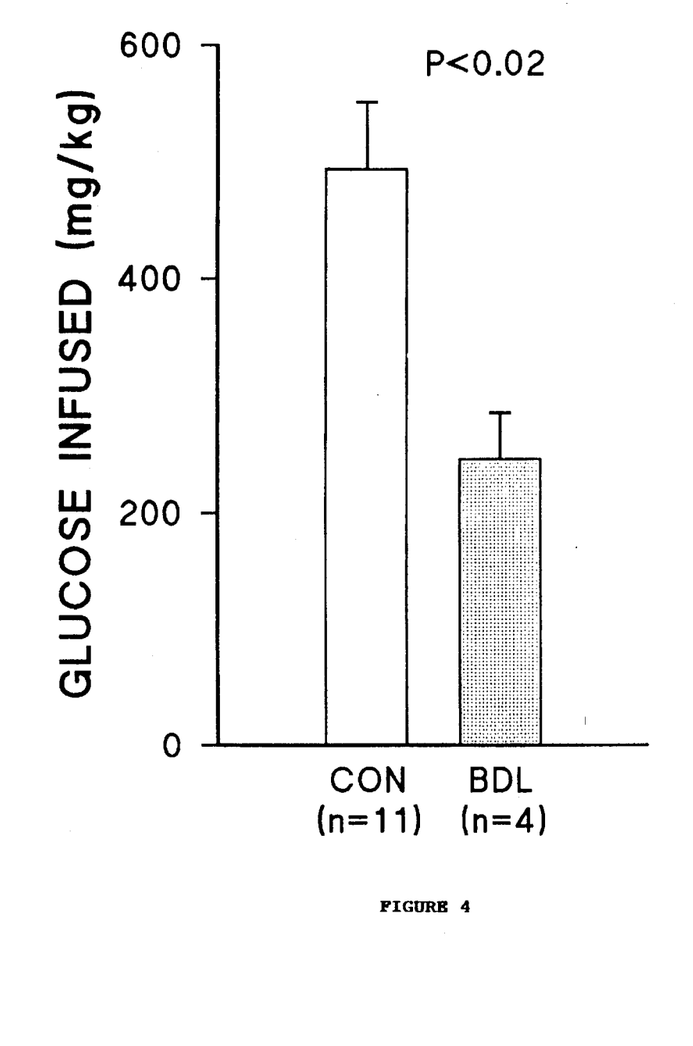
FIG. 4 shows insulin sensitivity of control (open bar) and bile duct ligated (shaded bar) rats.

At the end of three weeks, the insulin sensitivity of these animals was examined, after 100 mU/kg insulin, as described in Example 1. 11 control animals were also examined for insulin sensitivity. The results are shown in FIG. 4. Insulin sensitivity was reduced by about 50% in all bile duct ligated animals ($p<0.02$).

EXAMPLE 6

Insulin resistance produced by carbon tetrachloride.

2 rats were given 1 ml/kg $CCl_4$ on day 1, followed by 0.25 ml/kg $CCl_4$ administered by gavage every second day, excluding weekends, for a 3 week period. 2 days after the last $CCl_4$ administration, insulin sensitivity was tested as described in Example 1, after 100 mU/kg insulin.

Figure 5:
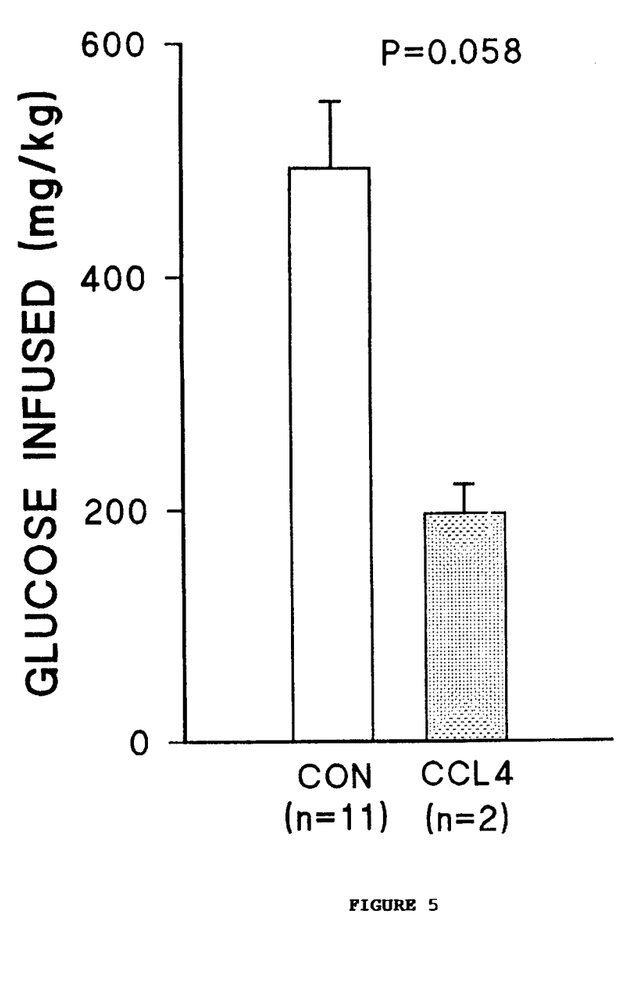
FIG. 5 shows insulin sensitivity of control (open bar) and $CCL_4$ treated (shaded bar) rats.

Results are shown in FIG. 5. Insulin sensitivity was reduced by about 60% in the $CCl_4$-treated rats ($p=0.058$).

EXAMPLE 7

Reversal of bile duct ligation-induced resistance by acetylcholine

One rat which had been subjected to chronic bile duct ligation, as described in example 5, was treated with acetylcholine in the manner and dosage described in Example 3, and its insulin sensitivity was determined as described in Example 1, after administration of 100 mU/kg insulin. As seen in FIG. 6, the insulin resistance produced by chronic bile duct ligation was significantly reversed by acetylcholine treatment.

EXAMPLE 8

A cat was anesthetized with pentobarbital and a brachial venous catheter was used for administration of fluids and supplemental anesthetic. Anesthetic was delivered by constant drip to avoid the disruption in glucose homeostasis seen when using small bolus supplementation. Systemic arterial pressure was monitored through a femoral arterial catheter. Fluids were administered by drip throughout the experiment to maintain arterial and central venous pressure. Blood gases and pH were monitored on a routine basis. Body temperature was monitored and maintained at 37.5° C. Arterial blood samples were taken from a second femoral catheter and venous blood samples were taken through a femoral venous catheter. A second femoral venous catheter was used to continuously monitor central venous blood pressure.

The euglycemic clamp was maintained by determining blood glucose levels at 3 minute intervals using 0.1 ml of whole blood assayed using a glucose oxidase membrane methodology (YSI Industrial Analyzer). responses were not initiated until 30 minute of constant arterial glucose levels were attained. Following the test injection of insulin or cholinergic agents, glucose infusions were adjusted using a continuously variable pump in order to maintain the arterial glucose concentration at the control level. The response was quantified according to the amount of glucose required for infusion over a 60 minute period.

Figure 7:
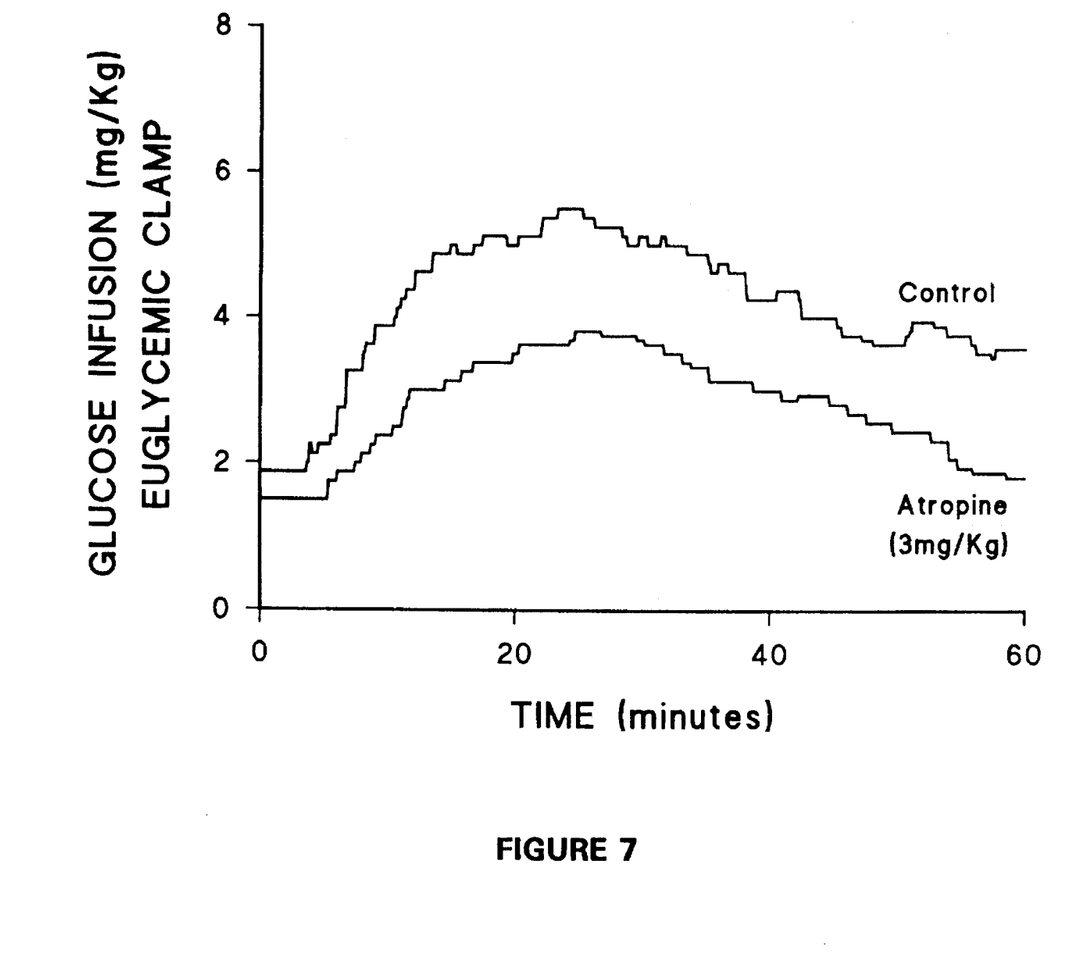
FIG. 7 shows pattern of glucose infusion to maintain constant blood glucose level in control and atropine-treated cats.

The results are shown in FIG. 7 which shows the pattern of glucose infusion required to maintain the blood glucose level constant in the control state and after 3 mg/kg atropine injected into the portal vein in 8 cats.

EXAMPLE 9

8 cats were treated with sequential intraportal injections of atropine. Results are shown in FIG. 8 which shows the dose-related production of insulin resistance produced by the sequential atropine injections.

It is significant that the atropine administration with the euglycemic clamp results in a similar degree of insulin resistance in the absence of the hypoglycemic response. This removes the likelihood that hepatic afferent nerves are responding to intrahepatic hypoglycemia to produce a counterregulatory response.

Figure 8:
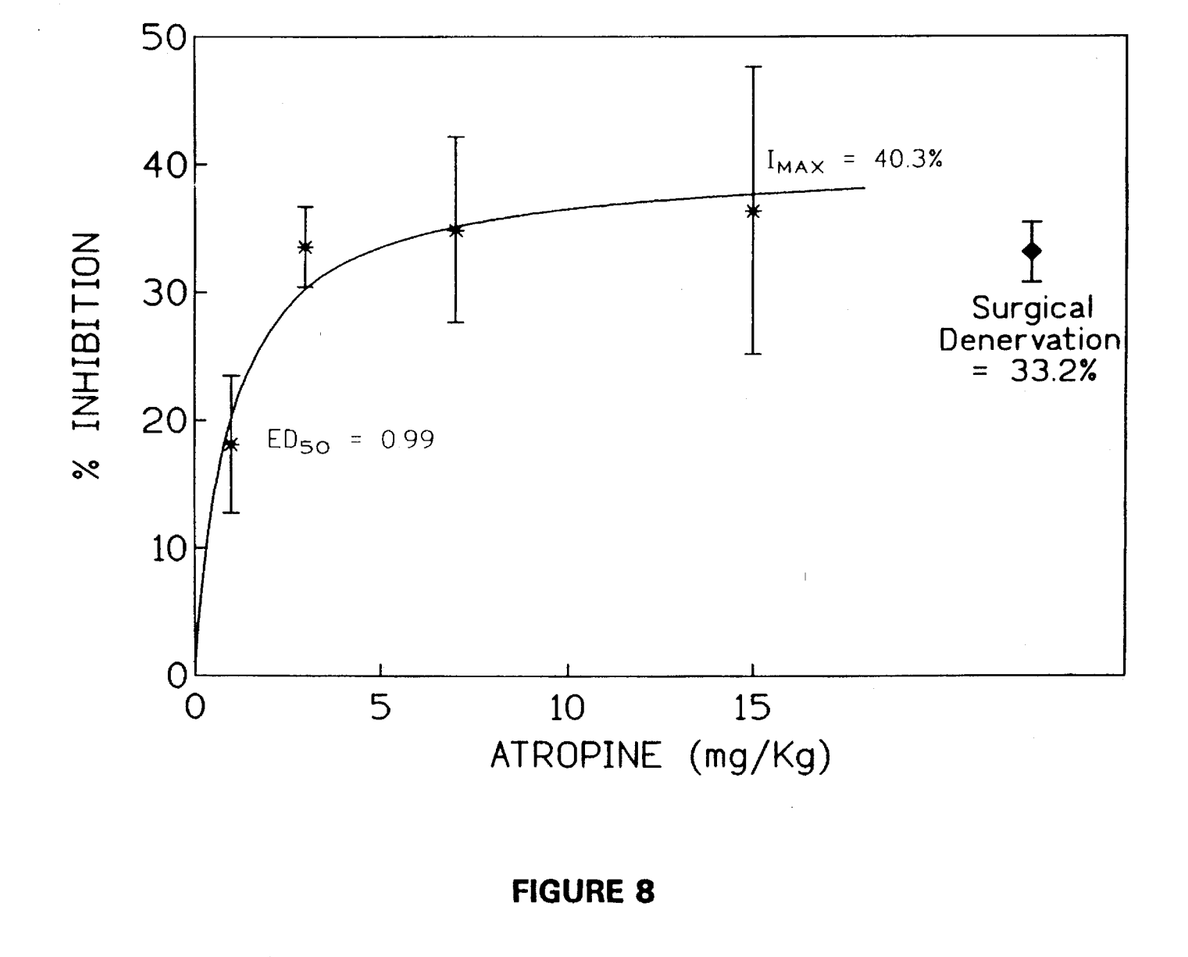
FIG. 8 shows production of insulin resistance after sequential atropine injections in the cat.

The insulin resistance produced was very similar to that produced by hepatic denervation (FIG. 8). The results further suggest that the insulin resistance reaches a maximal level following the administration of 2 mg/kg of atropine. Because of the long half-life of atropine, such sequential dose administration results in additive effects of each subsequent administration so that it appears that a total dose of 3 mg/kg will produce the maximum degree of insulin resistance. Time control studies have shown that at least five consecutive control responses can be demonstrated to be reproducible in the absence of other experimental interventions in cats.

The similarity of insulin resistance in the bodies of rats and cats produced by same mechanism strongly suggests that such a mechanism also operates in humans and that compounds effective to treat this resistance in the animal model will be effective also in the human.

References:

Brown, M. J. and Asbury, A. K. Diabetic neuropathy. Ann. Neurol. 15:2–12, 1984.

d'Almeida, M. S. and Lautt, W. W. Effect of bile ductligation on the hepatic venous system and vascular reactivity in the cat. Gastroenterology (submitted), 1993.

DeFronzo, R. A., Ferrannini, E., Hendler, R., Wahren, J., and Felig, P. Influence of hyperinsulinemia, hyperglycemia, and the route of glucose administration on splanchnic glucose exchange. Proc. Natn. Acad. Sci. U.S.A. 75:5173–5177, 1978a.

DeFronzo, R. A., Ferrannini, E., Wahren, J., and Felig, P. Lack cf gastrointestinal mediator of insulin action in maturity-onset diabetes. Lancet 1978:1077–1079, 1978b.

Felig, P., Wahren, J., and Hendler, R. Influence of oral glucose ingestion on splanchnic glucose and gluconeogenic substrate metabolism in man. Diabetes 24: 468–475, 1975.

Felig, P., Wahren, J. and Hendler, R. Influence of maturity-onset diabetes on splanchnic glucose balance after oral glucose ingestion. Diabetes 27:121–126, 1978.

Fischer, U. Reflex mechanism of insulin secretion. Exp. Endocr. Bratisl. 8:137–146, 1974.

Fischer, U. Hommel, H. Zeigler, M. , and Micheal, R. The mechanism of insulin secretion after oral glucose administration. Diabetologia 8:107–110, 1972.

Forssmann, W. G. and Ito, S. Hepatocyte innervation in primates. J. Cell. Biol. 74:229–313, 1977.

Hosking, D. J., Bennett, T., and Hampton, J. R. Diabetic autonomic neuropathy. Diabetes 27:1043–1054, 1978.

Lautt, W. W. Autonomic neural control of liver glycogen metabolism. Med. Hypoth. 5:1287–1296, 1979.

Lautt, W. W. Hepatic parasympathetic neuropathy as cause of maturity-onset diabetes? Gen. Pharmac. 11:343–451 1980.

Lautt, W. W. Hepatic nerves—a review of their functions and effects. Can. J. Physiol. Pharmacol. 58:105–123, 1980.

Lautt, W. W. Carotid sinus baroreceptor effects on cat livers in control and hemorrhaged state. Can. J. Physiol. Pharmacol. 60:15921602, 1982.

Lautt, W. W. Afferent and efferent neural roles in liver function. Prog. Neurobiol. 21:323–348, 1983.

Lautt, W. W., Brown, L. C., and Durham, i.s. Active and passive control of hepatic blood volume responses to hemorrhage at normal and raised hepatic venous pressure in cats. Can. J. Physiol. Pharmacol. 58:1049–1057, 1980.

Lautt, W. W. and Carroll, A. M. Evaluation of topical phenol as a means of producing autonomic denervation of the liver. Can. J. Physiol. Pharmacol. 62:849–853, 1984.

Lautt, W. W. and Cote, M. G. Functional evaluation of 6hydroxydopamine-induced sympathectomy in the liver of the cat. J. Pharmacol. Exp. Ther. 198:562–567, 1976.

Lautt, W. W. and Cote, M. G. The effect of 6hydroxydopamine-induced hepatic sympathectomy on the early hyperglycemic response to surgical trauma under anesthesia. J. Trauma 17:270–274, 1977.

Lautt, W. W. and Wong, C. Hepatic parasympathetic neural effect on glucose balance in the intact liver. Can. J. Physiol. Pharmacol. 56:679–682, 1978.

Lickley, H. L. A., Chisholm, O. J., Rabinovich, A., Wexler, M., and Dupre, J. Effects of portocaval anastomosis on glucose tolerance in dogs: evidence of an interaction between the gut and the liver in oral glucose disposal. Metabolism 24:1157–1168, 1975.

Menzinger, G., Gambardella, S., Spallone, V., and Felici, M. G. Recent developments in diabetic autonomic neuropathy. Diabet. Comp. 69:259–282, 1991.

Moncada, S. and Palmer, R. M. J. Inhibition of the induction of nitric oxide synthase by glucocorticoids: yet another explanation for their anti-inflammatory effects? TIPS 12:130–131, 1991.

Moncada, S., Palmer, R. M. J., and Higgs, E. A. Nitric oxid physiology, pathophysiology, and pharmacology. Pharmacol. Rev. 43(2):109–142, 1991.

Mondon, C. E. and Burton, S. D. Factors modifying carbohydrate metabolism and effect of insulin in perfused rat liver. Am. J. Physiol. 220:724–733, 1971.

Schafer, J., d'Almeida, M. S., Weisman, H., and Lautt, W. W. Reduced hepatic blood volume responses to hemorrhage and nerve stimulation but normal compliance and norepinephrine effects in cats with chronic bile duct ligation. Hepatology (in press), 1993.

Sharma, K. N. and Nasset, E. S. Electrical activity in mesenteric nerves after perfusion of gut lumen. Am. J. Physiol. 202:725–730, 1962.

Shimazu, T. Regulation of glycogen metabolism in liver by the autonomic nervous system. V. Activation of glycogen synthetase by vagal stimulation. Biochim. Diophys. Acta 252:28–38, 1971.

Shimazu, T. Glycogen synthetase activity in liver: regulation by the autonomic nerves. Science 156:1256–1257, 1974.

Shimazu, T. and Fujimoto, T. Regulation of glycogen metabolism in liver by the autonomic nervous system. IV. Neural control of glycogen biosynthesis. Biochem. Biophys. Acta 252:18–27, 1971.

Shimazu, T., Fukuda, A., and Ban, T. Reciprocal influences of the ventromedial and lateral hypothalamic nuclei on blood glucose level and liver glycogen content. Nature 210:1178–1179, 1966.

Xie, H., Tsybenko, V. A., Johnson, M. V., and Lautt, W. W. Insulin resistance of glucose response produced by hepatic denervations. Can. J. Physiol. Pharmacol. 71(2):175–178, 1993.

Yagihashi, S. and Simar, A. A. F. Diabetic autonomic neuropathy in BB rat: ultrastructural and morphometric changes in parasympathetic nerves. Diabetes 35(7):733–43, 1986.

Collins et al., (1970), Arch. Intern. Med., v. 126, pp. 608–614.

Bergman et al., (1985), Endocrine Rev., v. 6, pp. 45–86.

Shankar et al., (1987), Am. J. Physiol., v. 252, E772–E777.

Creutzfeld et al., (1983), In Liver in Metabolic Diseases, eds. Blanchi et al., pp. 221–234.

Taylor et al., (1986), Clin. Sci. (Lond.), v. 70, pp. 317–320.

De Fronzo et al., (1981), Diabetes, v. 30, pp 1000–1007.

Lee et al., (1992), Gut, v. 33, pp. 87–91.

Akiyoshi, J., (1989), Virchows Arch. B. Cell Pathol., v. 57, pp 81–90.

We claim:

1. A method for increasing insulin responsiveness and improving glucose tolerance in a mammal in which insulin responsiveness and glucose tolerance are impaired comprising administering to the mammal an effective amount of a cholinergic agonist.

2. A method in accordance with claim 1 wherein the mammal is a human patient suffering from non-insulin dependent diabetes mellitus.

3. A method in accordance with claim 2 wherein the cholinergic agonist is administered orally.

4. A method in accordance with claim 3 wherein the cholinergic agonist is a muscarinic agonist.

5. A method in accordance with claim 2 wherein the cholinergic agonist is acetylcholine.

6. A method in accordance with claim 2 wherein the cholinergic agonist is methacholine or bethanechol.

7. A method in accordance with claim 1 wherein the mammal is a human patient with liver disease.

8. A method in accordance with claim 7 wherein the cholinergic agonist is acetylcholine.

9. A method in accordance with claim 7 wherein the cholinergic agonist is methacholine or bethanechol.

10. A method in accordance with claim 1 wherein the cholinergic agonist is selected from the group consisting of acetylcholine, methacholine and bethanechol.

11. A method for reducing insulin resistance in a mammal comprising administering to the mammal an effective amount of a cholinergic agonist.

12. A method in accordance with claim 11 wherein the mammal is a human patient suffering from non-insulin dependent diabetes mellitus.

13. A method in accordance with claim 11 wherein the mammal is a human patient with liver disease.

14. A method in accordance with claim 11 wherein the mammal is a human patient with chronic bile duct ligation.

15. A method in accordance with claim 11 wherein the cholinergic agonist is administered orally.

16. A method in accordance with claim 11 wherein the cholinergic agonist is selected from the group consisting of acetylcholine, methacholine and bethanechol.

17. A method in accordance with claim 11 wherein the cholinergic agonist is acetylcholine.

18. A method in accordance with claim 11 wherein the cholinergic agonist is methacholine or bethanechol.

* * * * *